US00PP31968P2

(12) United States Plant Patent
LaBonte

(10) Patent No.: US PP31,968 P2
(45) Date of Patent: Jul. 14, 2020

(54) SWEETPOTATO PLANT NAMED 'LA17-120'

(50) Latin Name: ***Ipomoea batatas* (L.) Lam.**
Varietal Denomination: LA17-120

(71) Applicant: The Board of Supervisors of Louisiana State University and Agricultural and Mechanical College, Baton Rouge, LA (US)

(72) Inventor: Don R. LaBonte, Baton Rouge, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

(21) Appl. No.: 16/350,994

(22) Filed: Feb. 8, 2019

(51) Int. Cl.
*A01H 5/12* (2018.01)
*A01H 6/00* (2018.01)

(52) U.S. Cl.
USPC ..... Plt./258

(58) Field of Classification Search
USPC ..... Plt./258
See application file for complete search history.

*Primary Examiner* — Susan McCormick Ewoldt
*Assistant Examiner* — Karen M Redden
(74) *Attorney, Agent, or Firm* — Baker Donelson

(57) ABSTRACT

A new variety of sweetpotato, identified as 'LA17-120', is disclosed having resistance to southern root-knot nematode; a purple flesh storage root and attractive 5-lobed green leaves with purple vines.

3 Drawing Sheets

Genus and species name: *Ipomoea batatas* (L.) Lam.
Variety denomination: 'LA17-120'.

BACKGROUND OF THE INVENTION

Sweetpotatoes, unlike Irish potatoes (*Solanum tuberosum*), are not tuber propagated plants. A "tuber" is a short, thickened portion of an underground branch. Along a tuber "eyes" are found, each of which comprises a ridge bearing a scale-like leaf (analogous to a branch leaf) having minute meristematic buds in the axial of the leaf. By contrast, sweetpotato roots are developmentally and anatomically true roots, lacking meristematic buds, and are not derived from an underground branch. Sweetpotatoes do not form tubers.

SUMMARY OF THE INVENTION

This invention pertains to a new and distinct variety of sweetpotato. This new and distinct sweetpotato variety demonstrates intermediate to susceptible disease resistance to *Fusarium* wilt and resistance to southern root-knot nematode, and has ornamental foliage characteristics. It also demonstrates a purple flesh storage root and 5 lobed leaf in comparison to '05-111' with an entire leaf, orange flesh storage roots and a copper skin.

DETAILED BOTANICAL DESCRIPTION

This new variety of sweetpotato, named 'LA17-120', resulted from an open-pollinated cross performed in 2016 to the female parent 'LA15-536' (not patented). 'LA17-120' was developed to provide a variety with storage root characteristics similar to '05-111' (U.S. Plant Pat. No. 23,761 P3), but with purple flesh storage root and attractive foliage for ornamental use. 'LA15-536' has white fleshed storage roots and differs from 'LA17-120' which has purple fleshed storage roots.

Plants of 'LA17-120' and variety '05-111' can be differentiated. Leaves of 'LA17-120' are five-lobed. '05-111' has an entire leaf with no lobes. Roots of 'LA17-120' have purple skin [2.5 R (red) R (purple) (2/6)] and can be differentiated from the light to medium rose skin of '05-111'. Color terminology used herein is in accordance with the MUNSELL® Book of Color (2003 Edition, Munsell Color, GretagMacbeth LLC, 617 Little Britain Road, New Windsor, N.Y. 12553-6148). The color descriptions and color illustrations are as nearly true as is reasonably possible. However, it is understood that both color and other phenotypic expressions described herein may vary from plant to plant with differences in growth, environment and cultural conditions, without any change in the genotype of the variety 'LA17-120'.

'LA17-120' roots were stored during the winter in Chase, La. 'LA17-120' was planted the following spring, resulting in approximately 8-10 sprouts per root. Cuttings from the sprouts were transplanted successfully for asexual reproduction in Chase, La. Asexual propagation of the new cultivar by cuttings has shown that the unique features of this new sweetpotato were stable and that the plant reproduced true to type in successive generations of asexual propagation. Plants described herein were 90 days in age from planting in full sun field plantings.

Figure 1:
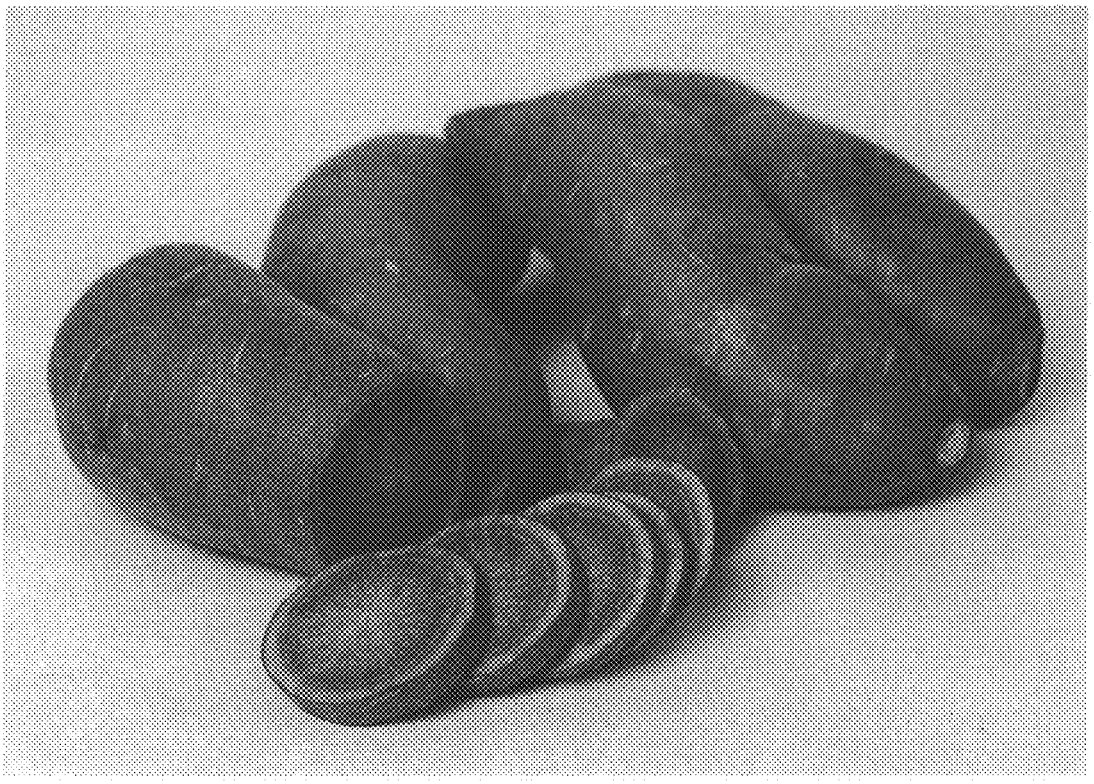
FIG. 1 is a color photograph of the fleshy root form of the novel variety of sweetpotato identified as 'LA17-120'.
Figure 2:
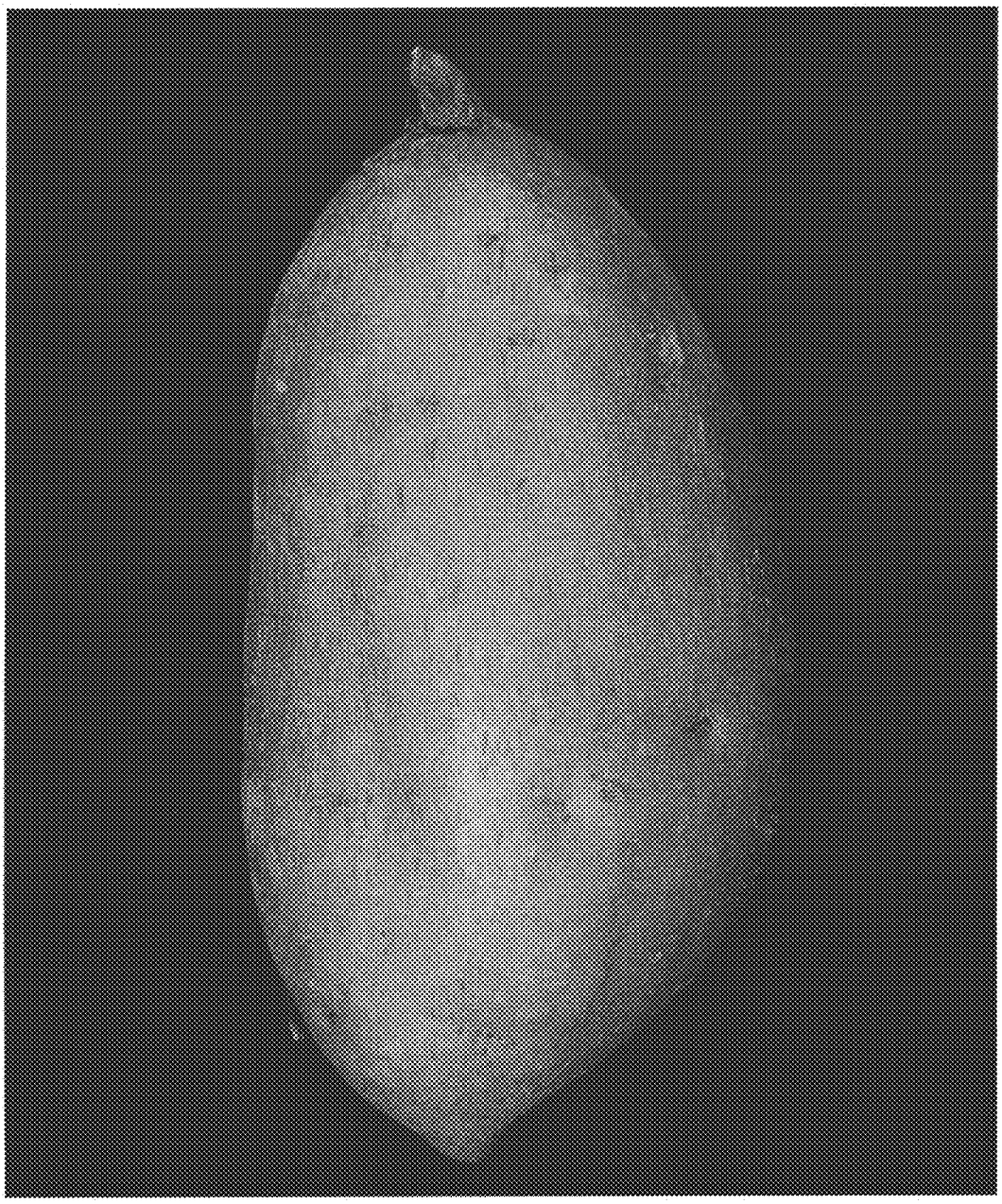
FIG. 2 is a color photograph of the fleshy root form of the sweetpotato variety identified as '05-111'.

FIG. 1 depicts the fleshy root form of the 'LA17-120' sweetpotato. The skin is purple and differs from the light to medium rose '05-111', both at harvest and after several months of storage as shown in Table 1. MUNSELL® Book of Color values for skin and flesh for both 'LA17-120' and '05-111' storage roots are shown in Table 1. The '05-111' sweetpotato is depicted in FIG. 2. The skin for both 'LA17-120' and '05-111' was smooth. The 'LA17-120' cortex was 5.2 mm in depth and the color similar throughout. The flesh of 'LA17-120' is purple in comparison to orange flesh '05-111'.

TABLE 1

| Variable | Variety | Color |
|---|---|---|
| Skin | 'LA17-120' | 2.5 R (red) P (purple) 2/6 |
| | '05-111' | 2.5 Y (yellow) R (red) 6/6 |
| Flesh | 'LA17-120' | 2.5 R (red) P (purple) 4/6 |
| | '05-111' | 2.5 Y (yellow) R (red) 7/8 |

Figure 3:
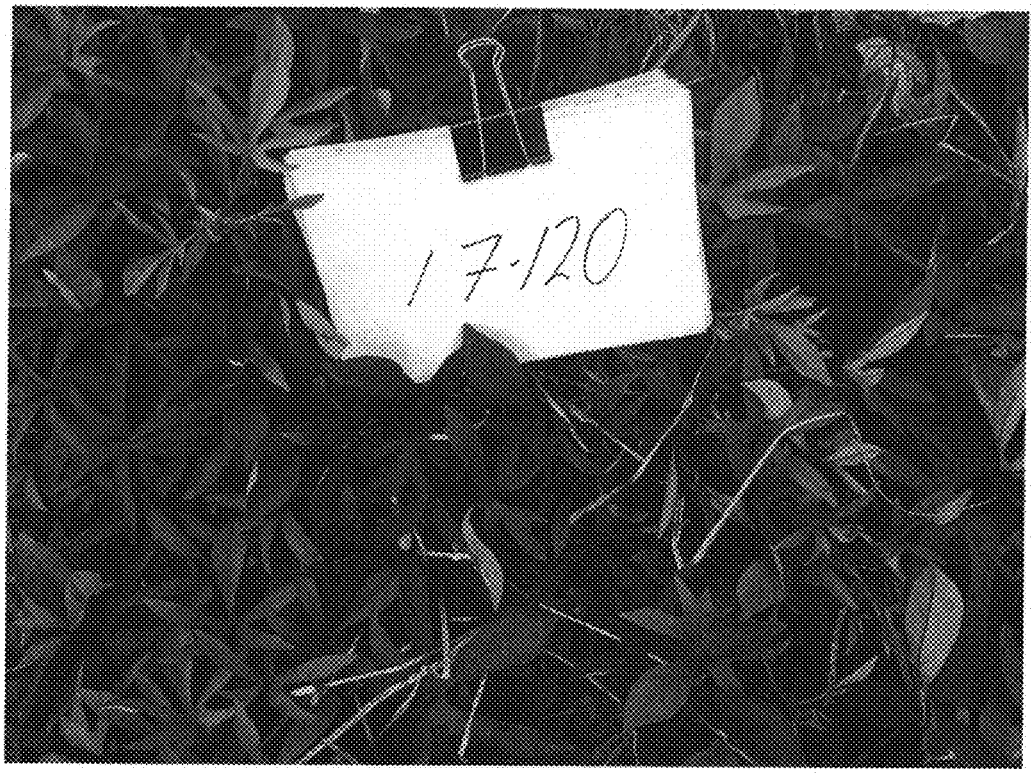
FIG. 3 is a color photograph of the canopy biomass of the novel variety of sweetpotato identified as 'LA17-120'.

FIG. 3 depicts the canopy biomass of 'LA17-120' sweetpotato. 'LA17-120' has round, green-stemmed vines which change [2.5 G (green) Y (yellow) (5/8)] to purple vines [2.5 R (red) P (purple) (3/4)] 15 cm from the apex and extends to the crown of the roots. The first 4 cm from the apex is slightly pubescent becoming more densely pubescent on young vine tissue. The 'LA17-120' canopy biomass appears similar to '05-111'. The 'LA17-120' canopy architecture was 25 cm in height from the soil surface. For 'LA17-120', six main vines arose from the main stem near the soil surface. The stem giving rise to these vines was 1.6 cm in diameter; the 6 lateral vines were 76 cm in length with diameters of about 0.5 cm at 65 cm from the base and diameters of about 0.5 cm at the first internode of the first fully developed leaf from the apex. Six lateral branches arose from each of the main vines. At the first internode from the apex, the internode length was about 2.8 cm between the first and second fully developed leaves. Internode lengths for other sections of the vine averaged about 6 cm. Unfolded immature leaves were light green [2.5 G (green) Y (yellow) (5/8)] for the adaxial and abaxial surface, which change over one node from the apex for the adaxial surface to a green upper surface [7.5 G (green) Y (yellow) (4/6)] and a light green [7.5 G (yellow) Y (yellow) (5/4)] abaxial surface. Mature leaves five nodes from the apex had an acute apex and mostly a cordate base and medium to deep 5 lobed lamina. Abaxial and adaxial lamina surfaces are smooth. Leaf margins are entire. Mature leaves were about 8.3 cm long and 13.2 cm wide. Adaxial and abaxial veins were in a pinnate venation pattern and purple [7.5 R (red) P (purple) (2/4)]. The petiole was purple [7.5 R (red) P (purple) (2/4)]. The coloration extended from the leaf veins to the petiole in a continuous fashion. The petiole was 13.5 cm long at five nodes from the apex, and 3 mm in diameter at 5 cm from the leaf junction. The dormant nodal meristem was purple [7.5 R (red) P (purple) (2/4]. Stipules are not present.

'LA17-120' is heavy flowering. A typical inflorescence of 'LA17-120' displayed two clusters of three flowers per peduncle. The width of the inflorescence is 2.6 cm wide and 4.0 cm long (no flowers extended from calyx) and were purple [7.5 R (red) P (purple) (2/4)]. Pedicles were 1.2 cm long and 2 mm wide and peduncles were 9-10 cm long, and about 3 mm in diameter. The pedicles changed from purple [7.5 R (red) P (purple) (2/4)] at the base to a green with a purple hue [2.5 G (green) Y (yellow) (5/4)] at the base of the flower. Individual flowers were about 3.7 cm long from the base of the calyx, and the corolla was 2.5-3.0 cm wide at the opening. The fused flower petals formed a pentagonal pattern with smooth edges. The inner throat of the corolla was purple [7.5 P (purple) (3/8)]. The inner and outer limbs of the corolla (corollas outermost area, distal from the calyx) were light purple [5 P (purple) (8/4)]. The inner and outer lamina of the corolla are smooth. The five sepals comprising the calyx were elliptic with a cordate apex and green with a purple hue [2.5 G (green) Y (yellow) (5/4)]; three of these sepals were about 12.5 mm long and 5.7 mm wide. Two other sepals (interspersed) were about 8 mm long and 4 mm wide. Sepal margins were smooth and inner and outer sepal lamina are smooth. The ovary was 3.4 mm round and green with a purple hue [2.5 G (green) Y (yellow) (5/4)]. The style was round, 1.1 cm long and light purple [5 P (purple) (8/4)] at the base and fades to white [Neutral 9.25] at the stigma. The stigma is 3.5 mm wide and 2 mm long. Five stamens were inferior to the stigmata. The filament was round, 0.6 cm long and light purple [5 P (purple) (8/4)] at the base and fades to white [Neutral 9.25] at the anther. The anther is 3.8 mm long. A slight fragrance was present. The anther and pollen are white [Neutral 9.25]. Mature seed capsules are round and 6.3 mm in length and width, and seeds are 3.5 mm round. One black [neutral 1.75] seed is produced on average per capsule.

EXAMPLE 1

Tests Conducted

To confirm that 'LA17-120' was a new ornamental variety with storage roots, controlled tests (e.g., pathogen responses and yield) were conducted in Baton Rouge, La. '05-111' was selected for comparison because of its importance in commercial United States orange flesh sweetpotato acreage. Diseases that commonly affect the growth of sweetpotatoes were selected to test for pathogen responses in both varieties. 'LA17-120' was intermediate to susceptible and '05-111' was resistant to *Fusarium* wilt or stem rot caused by *Fusarium oxysporum* Schlect. f sp. *batatas* (Wollenw.) Snyd. & Hans.

Nematode reproduction was measured in greenhouse tests. 'LA17-120' was resistant while '05-111' was susceptible to race 3 of the southern root-knot nematode, *Meloidogyne incognita* (Kofoid & White 1919) Chitwood 1949.

'LA17-120' is drought and heat tolerant like '05-111' and succumbs to death at freezing like '05-111'.

'LA17-120' has not been tested for novel insect resistance.

To determine yield production, complete-block trials using three replications of 'LA17-120' and '05-111' were conducted in 2018 in Louisiana, Arkansas and South Carolina. 'LA17-120' and '05-111' sweetpotato plants were transplanted in randomized complete-block trials at 31-cm spacings. Each block/plot was fertilized with approximately 250 pounds per acre of a mixed fertilizer comprising 13% N, 13% $P_2O_5$, and 13% $K_2O$. 'LA17-120' was compared to '05-111' at transplanting dates in June. Average yields were measured for the following grades of roots: U.S. #1 (51-89 mm in diameter, 76-229 mm long); Canner (25-51 mm in diameter, 51-178 mm long); and Jumbo (larger than U.S. #1 in diameter, length or both, and without objectionable defects). A typical marketable root of 'LA17-120' was 180-190 mm long, 60-70 mm in diameter, mostly round-elliptic in shapes. The base or distal end tended to be more elongated in comparison to slightly rounder apex (proximal end). U.S. #1 roots typically weighed 150-190 g A mid-season transplanting date trial was conducted at Gilbert, La. in 2018. 'LA17-120' and '05-111' were transplanted on Jun. 19, 2018 and harvested on Oct. 19, 2018 (123 days after planting). Average yields, measured as Metric Tons per Hectare ($MT \cdot ha^{-1}$), for 'LA17-120' and '05-111' are shown in Table 2.

TABLE 2

Mid-season transplant date yield trial.

| Selection | US#1† | Canners† | Jumbos† | TMY‡† |
|---|---|---|---|---|
| 'LA17-120' | 6.35a | 9.76a | 0.00a | 16.11a |
| '05-111' | 10.98a | 11.23a | 0.00a | 22.21a |

†Average yields in $MT\text{-}ha^{-1}$ of varieties followed by a common letter do not differ significantly ($P < 0.05$) according to Duncan's Multiple Range Test.
TMV‡ = total marketable yield A mid-season transplanting date trial was also conducted at Wynne, Ark. in 2018. 'LA17-120' and '05-111' were transplanted on Jun. 5, 2018 and harvested on Oct. 9, 2018 (127 days after planting). Average yields, measured as Metric Tons per Hectare ($MT \cdot ha^{-1}$), for 'LA17-120' and '05-111' are shown in Table 3.

TABLE 3

Mid-season transplant date yield trial.

| Selection | US#1† | Canners† | Jumbos† | TMY‡† |
|---|---|---|---|---|
| 'LA17-120' | 7.73a | 9.63a | 8.48a | 25.82a |
| '05-111' | 16.5a | 11.04a | 8.74a | 36.25a |

†Average yields in $MT\text{-}ha^{-1}$ of varieties followed by a common letter do not differ significantly ($P < 0.05$) according to Duncan's Multiple Range Test.
TMY‡ = total marketable yield A mid-season transplanting date trial was also conducted at Windsor, S.C. in 2018. 'LA17-120' and '05-111' were transplanted on Jun. 14, 2018 and harvested on Oct. 22, 2018 (131 days after planting). Average yields, measured as Metric Tons per Hectare ($MT \cdot ha^{-1}$), for 'LA17-120' and '05-111' are shown in Table 4.

TABLE 4

Mid-season transplant date yield trial.

| Selection | US#1† | Canners† | Jumbos† | TMY‡† |
|---|---|---|---|---|
| 'LA17-120' | 5.77a | 53.17a | 0.0a | 58.94a |
| '05-111' | 12.44a | 13.67a | 0.77a | 26.89a |

†Average yields in $MT\text{-}ha^{-1}$ of varieties followed by a common letter do not differ significantly ($P < 0.05$) according to Duncan's Multiple Range Test.
TMY‡ = total marketable yield As shown in Tables 2-4, 'LA17-120' produced mostly lower total yield in comparison to '05-111' in regional trials at various planting dates. 'LA17-120' had harvestable roots approximately 120-130 days after planting, which is typical development time for sweetpotatoes and comparable to '05-111'. 'LA17-120' is not intended for commercial production but intended as an ornamental.

'LA17-120' should be a valuable commercial ornamental sweetpotato variety. 'LA17-120' has lower yield in comparison to '05-111' and represents a unique canopy type which produces edible purple roots.

I claim:

1. A new and distinct variety of *Ipomoea batatas* plant named 'LA17-120' as described and illustrated in the specification herein.

* * * * *